(12) United States Patent
Gross et al.

(10) Patent No.: US 6,784,178 B2
(45) Date of Patent: Aug. 31, 2004

(54) PHARMACOTHERAPY FOR VASCULAR DYSFUNCTION ASSOCIATED WITH DEFICIENT NITRIC OXIDE BIOACTIVITY

(75) Inventors: Steven S. Gross, New York, NY (US); Caroline L. Jones, Nottingham (GB)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 10/240,729

(22) PCT Filed: Apr. 3, 2001

(86) PCT No.: PCT/US01/08635

§ 371 (c)(1),
(2), (4) Date: Oct. 9, 2002

(87) PCT Pub. No.: WO01/78717

PCT Pub. Date: Oct. 25, 2001

(65) Prior Publication Data

US 2003/0212135 A1 Nov. 13, 2003

Related U.S. Application Data

(60) Provisional application No. 60/196,298, filed on Apr. 12, 2000.

(51) Int. Cl.[7] .................... A61K 31/50; A61K 31/195; A61K 31/155
(52) U.S. Cl. ................ 514/249; 514/565; 514/634
(58) Field of Search ................. 514/249, 565, 514/634

(56) References Cited

U.S. PATENT DOCUMENTS

| | | | |
|---|---|---|---|
| 5,028,627 A | 7/1991 | Kilbourn et al. | 514/565 |
| 5,059,712 A | 10/1991 | Griffith | 562/560 |
| 5,158,883 A | 10/1992 | Griffith | 435/240.2 |
| 5,216,025 A | 6/1993 | Gross et al. | 514/565 |
| 5,217,997 A | 6/1993 | Levere et al. | 514/565 |
| 5,281,627 A | 1/1994 | Griffith | 514/565 |
| 5,380,945 A | 1/1995 | Murad et al. | 564/108 |
| 5,478,946 A | 12/1995 | Murad et al. | 548/215 |
| 5,543,430 A | 8/1996 | Kaesemeyer | 514/565 |
| 5,759,835 A | 6/1998 | Rosazza et al. | 435/189 |
| 5,945,452 A | 8/1999 | Cook et al. | 514/564 |
| 5,968,983 A | 10/1999 | Kaesemeyer | 514/564 |
| 6,028,054 A | 2/2000 | Benet et al. | 514/9 |
| 6,277,884 B1 * | 8/2001 | de Tejada | 514/565 |
| 6,436,997 B1 * | 8/2002 | de Tejada | 514/565 |

OTHER PUBLICATIONS

STN Monograph of RN 53054–07–2, Registry File for N.omega.–hydroxy–L–arginine.*

* cited by examiner

Primary Examiner—Raymond J. Henley, III

(57) ABSTRACT

A patient with a disorder involving endothelial dysfunction associated with deficient nitric oxide bioactivity, e.g., coronary artery disease, atherosclerosis, hypertension, diabetes or neurodegenerative condition stemming from ischemia and/or inflammation, is treated by administering nitric oxide bioactivity increasing hydroxyguanidine.

18 Claims, 5 Drawing Sheets

— BH4—bound eNOS

— +Sepiapterin

— +BH2

20G

PHARMACOTHERAPY FOR VASCULAR DYSFUNCTION ASSOCIATED WITH DEFICIENT NITRIC OXIDE BIOACTIVITY

The application is a filing under 35 U.S.C. 371 of PCT/US01/08635, filed 3 Apr. 2001, which claims the benefit of U.S. Provisional Application No. 60/196,298 filed 12 Apr. 2000; PCT/US01/08635 was published in English as WO 01/78717 on 25 Oct. 2001.

TECHNICAL FIELD

This invention is directed at enhancing vascular function in patients with vascular diseases and conditions that are associated with deficient nitric oxide bioactivity, endothelial dysfunction, tetrahydrobiopterin insufficiency and/or oxidative stress. In an embodiment the oxidative stress triggers the tetrahydrobiopterin insufficiency which in turn triggers deficient nitric oxide bioactivity and endothelial dysfunction, and the invention is directed at treating the vascular diseases and conditions associated with the endothelial dysfunction.

BACKGROUND OF THE INVENTION

It is known that nitric oxide is constitutively produced by vascular endothelial cells where it plays a key physiological role in the moment-to-moment regulation of blood pressure and vascular tone.

It is known that deficient nitric oxide bioactivity contributes to the pathogenesis of vascular dysfunctions, including coronary artery disease, atherosclerosis, hypertension, diabetic vasculapathy and neurodegenerative conditions stemming from ischemia and/or inflammation, and that such pathogenesis includes damaged endothelium, poor flow of oxygenated blood resulting in oxygen-deficient organs and tissues, elevated systemic vascular resistance (high blood pressure), vascular smooth muscle proliferation, progression of vascular stenosis and inflammation.

There is no current medically established solution for reversing or diminishing the deficiency in nitric oxide bioactivity. However, health food stores sell arginine and arginine-containing preparations as dietary supplements, and efficacy in reversing conditions associated with endothelial dysfunction has been suggested. Administration of tetrahydrobiopterin has also been suggested to increase nitric oxide bioactivity by blood vessels of chronic smokers and in animal models of atherosclerosis.

SUMMARY OF THE INVENTION

It has been discovered in the course of making the invention that a predominant reason for nitric oxide (NO) deficiency in disorders involving endothelial dysfunction associated with deficient nitric oxide bioactivity is that dihydrobiopterin ($BH_2$) binds to eNOS (an enzyme associated with constitutive nitric oxide production in endothelial cells of blood vessels) with affinity equal to the natural cofactor tetrahydrobiopterin ($BH_4$), but that whereas $BH_4$-bound eNOS mediates production of nitric oxide, $BH_2$-bound eNOS does not. Rather $BH_2$-bound eNOS causes diminished nitric oxide to be present by producing superoxide anion that reacts with nitric oxide to inactivate it. $BH_2$-bound eNOS also causes a cascade effect by producing superoxide anion which oxidizes $BH_4$ to $BH_2$ and still greater rate of superoxide production and further diminished production of nitric oxide and increased inactivation of nitric oxide. Oxidative conditions that can predominate in vascular disorders can oxidize $BH_4$ to $BH_2$, thereby initiating this cascade. It is also discovered in the course of making the invention herein that hydroxyarginine, and other hydroxyguanidine-containing molecules can be metabolized to nitric oxide by $BH_2$-bound eNOS.

The invention herein is directed to a method of treating a patient with a disorder involving endothelial dysfunction associated with deficient nitric oxide bioactivity by restoring or increasing nitric oxide bioactivity in the patient and comprises administering to the patient a therapeutically effective amount of nitric oxide bioactivity increasing agent selected from the group consisting of nitric oxide bioactivity increasing hydroxyguanidines and pharmaceutically acceptable salts thereof, optionally in combination with arginine and/or tetrahydrobiopterin, thereby increasing or restoring nitric oxide bioactivity.

The endothelial dysfunction referred to is diagnosed by the failure of intracoronary infusion of 1 $\mu$mol/liter of acetylcholine in physiological saline to elicit an increase in coronary artery luminal diameter in a patient undergoing coronary angiography. An alternative non-invasive approach to assess endothelial dysfunction may be performed by measurement of flow-mediated vasodilation of the brachial artery using an ultrasound-based imaging technique. For this test, forearm brachial artely diameter is determined by ultrasound in the patient prior to testing. Subsequently, a pneumatic tourniquet is placed below the patient's elbow, inflated to 300 mm Hg and held at this pressure for 5 minutes. The tourniquet is then rapidly released and the flow-induced increase in luminal diameter is recorded at 1 min after release. If the observed flow-induced increase in luminal diameter averages 5% or less with 4 repeat measurements, a diagnosis of endothelial dysfunction is made.

The deficiency in nitric oxide bioactivity referred to above is due to oxidative stress which oxidizes some of the normally present nitric oxide and/or oxidizes tetrahydrobiopterin cofactor for nitric oxide production making it inactive, so as to deplete nitric oxide bioactivity.

BRIEF DESCRIPTION OF THE DRAWINGS

FIG. 2(*b*) shows electron paramagnetic resonance results that assess superoxide production by sepiapterin-bound eNOS in assay buffer.

FIG. 2(*c*) shows electron paramagnetic resonance results of superoxide production by $BH_2$-bound eNOS in assay buffer.

FIG. 3(*b*) is a graph showing $BH_2$-bound eNOS production of total nitrate/nitrite from arginine in assay buffer without NMA, denoted "Control"; with NMA, denoted "NMA"; and after elimination of calmodulin denoted "No CaM."

FIG. 3(*c*) is a graph showing $BH_4$-bound eNOS production of total nitrate/nitrite from $N^\omega$-hydroxyarginine in assay buffer without NMA, denoted "Control"; with NMA, denoted "NMA", and after elimination of calmodulin, denoted "No CaM."

Figure 1:
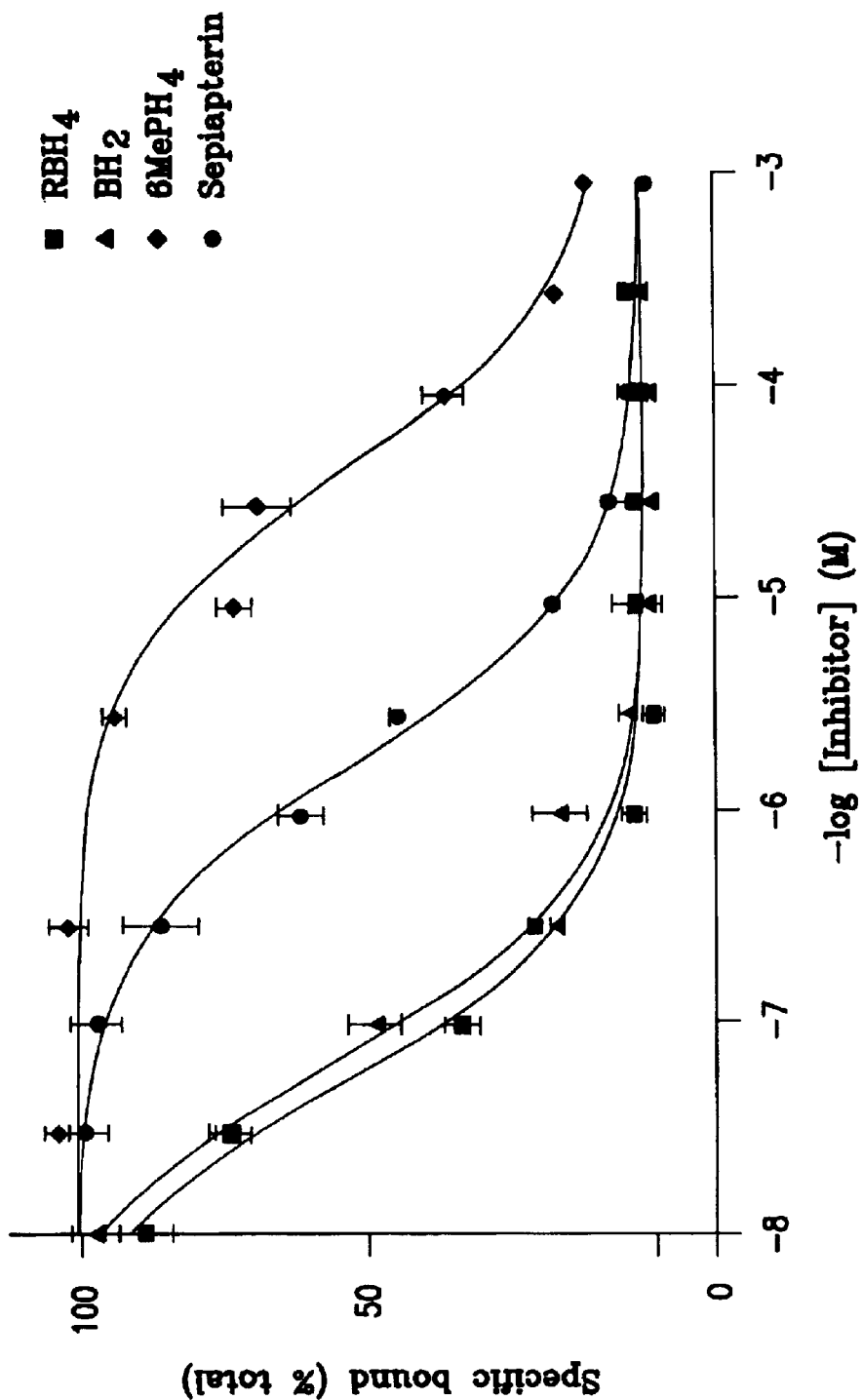
FIG. 1 is a graph which compares the affinity that the pterins 5,6,7,8-tetrahydrobiopterin ($BH_4$), 7,8-dihydrobiopterin ($BH_2$), 6-methyltetrahydrobiopterin ($6MePH_4$), and sepiapterin to compete for [$^3$H] tetrahydrobiopterin binding to eNOS.

The term "Specific Nitrite/Nitrate" in legends on FIGS. 3(a), 3(b), 3(c), 3(d) and 4 means the increase of nitrite/nitrate observed above background during the one hour incubation.

DETAILED DESCRIPTION

As indicated above, the method of the invention herein is for treating a patient with a disorder involving endothelial dysfunction associated with deficient nitric oxide bioactivity by restoring or increasing nitric oxide bioactivity in the patient and comprises administering to the patient a therapeutically effective amount of nitric oxide bioactivity increasing agent selected from the group consisting of nitric oxide bioactivity increasing hydroxyguanidines and pharmaceutically acceptable salts thereof optionally in combination with arginine and/or tetrahydrobiopterin, thereby increasing or restoring nitric oxide bioactivity.

Disorders involving endothelial dysfunction associated with deficient nitric oxide bioactivity are known and include coronary artery disease, atherosclerosis, hypertension, diabetes and neurodegenerative conditions stemming from ischemia and/or inflammation (e.g., inflammatory and neurodegenerative conditions owing to insufficient nitric oxide production, e.g., stroke).

We turn now to the agents which are selected from the group consisting of nitric oxide bioactivity increasing hydroxyguanidines and pharmaceutically acceptable salts thereof.

The nitric oxide bioactivity increasing hydroxyguanidines are preferably nitric oxide bioactivity increasing agents having the formula:

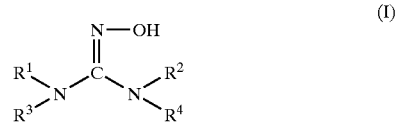

(I)

wherein $R^1$, $R^2$, $R^3$ and $R^4$ permit transport into cells and are the same or different and can be independently selected from the group consisting of hydrogen, amino, imino, alkyl, substituted alkyl, phenyl, substituted phenyl cycloalkyl, benzyl, acyl, pyridyl, piperidyl, piperazyl, amino acid, lipid and carbohydrate and wherein $R^3$ and $R^4$ can optionally join to form a ring. The alkyl can be, for example, $C_1$–$C_{10}$ alkyl. The substituents on substituted alkyl include, for example, one or more of the same or different of halo, thio, nitro, amino, carboxy, $C_1$–$C_6$ -alkoxy and aryl substituted on $C_1$–$C_{10}$ alkyl. The substituents on substituted phenyl include, for example, one or more of the same or different of halogen, $C_1$–$C_6$ alkyl, nitro, amino and $C_1$–$C_6$ alkoxy (e.g., methoxy). The cycloalkyl can contain, for example, from 3 to 8 carbon atoms. The acyl can be, for example, $C_1$–$C_6$ acyl. The halo and halogen include chloro, bromo and fluoro.

The pharmaceutically acceptable salts include, for example, the hydrochloride, acetate and sulfate salts. Other pharmaceutically acceptable salt group will be obvious to those skilled in the art.

Preferably at least one of $R^1$, $R^2$, $R^3$ and $R^4$ is hydrogen, and preferably two or three of $R^1$, $R^2$, $R^3$ and $R^4$ are hydrogen.

When one or both of $R^3$ and $R^4$ are alpha-amino acids, the alpha-amino acid can be an L-compound or D-compound or D,L-compound. L-compounds are preferably used but D-compounds and D,L-compounds also can be used.

The hydroxyguanidine treating agents include, for example, $N^\omega$-hydroxyarginine and hydroxyguanidine.

$N^\omega$-Hydroxyarginine has the formula (I) where $R^1$, $R^2$ and $R^3$ are hydrogen, and $R^4$ is $(CH_2)_3CH(NH_2)COOH$.

Hydroxyguanidine has the formula (I) where $R^1$, $R^2$, $R^3$ and $R^4$ are all hydrogen.

$N^\omega$-Hydroxyarginine and hydroxyguanidine are available commercially.

Still other hydroxyguanidine treating agents include, for example, compounds of formula (I) where $R^1$, $R^2$ and $R^3$ are H, and $R^4$ is $(CH_2)_3C(CH_3)(NH_2)COOH$, e.g., $N^\omega$-hydroxy-L-α-methylarginine; compounds of the formula (I) were $R^1$, $R^2$ and $R^3$ are H, and $R^4$ is $(CH_2)_4CH(NH_2)COOH$, e.g., $N^\omega$-hydroxy-L-homoarginine; compounds of the formula (I) where $R^1$, $R^2$ and $R^3$ are H, and $R^4$ is $(CH_2)_4NH_2$; and compounds of the formula (I) where $R^1$, $R^2$ and $R^3$ and H, and $R^4$ is $(CH_2)_4COOH$.

The other hydroxyguanidines are prepared by methods well known in the art from hydroxylamine or other simple precursors.

As indicated above, the agents are administered in therapeutically effective amounts, i.e., an endothelial dysfunction reversing or diminishing effective amount that provides reversal or diminishing or stopping of endothelial damage, increased oxygenated blood flow to oxygen-deficient organs and tissues, diminished vascular resistance (increased blood vessel dilation), reversing or stopping of progression of vascular stenosis and/or diminished inflammation. Therapeutic amounts depend on the agent administered and can range, for example, from 0.01 μmol/kg to 2 mmol/kg. For $N^\omega$-hydroxyarginine, administration can be, for example, of a loading dose, e.g., of 20 mg/kg, followed by 1 to 10 mg/kg/hr. Other suitable dosage information for $N^\omega$-hydroxyarginine is exemplified in the working examples hereinafter.

The routes of administration include oral, transdermal, intravenous, and intramuscular.

For transdermal administration, the agent can be administered, for example, as an ointment or cream containing from 0.1 to 3% of the agent.

Since the conditions treated are chronic, the administrations typically are on a daily basis.

The mode of benefit includes improved flow of oxygenated blood to oxygen-deficient organs and tissue, reduced systemic vascular resistance, diminished progression of vascular stenosis, and diminished inflammation.

We now turn to the optional case referred to above where agent as described above is used in combination with administration of arginine. The arginine used is L-arginine. The L-arginine is used in a therapeutically effective amount which is an amount effective to increase nitric oxide synthesis in vascular cells. This amount typically ranges from 5 to 20 grams per day. The-L-arginine is preferably administered orally.

We turn now to optional case referred to above where agent as described above is used in combination with administration of tetrahydrobiopterin. The tetrahydrobiopterin used is, for example, (6R)-5,6,7,8-tetrahydro-L-biopterin. The amount typically ranges from 0.05 mg/kg to 10 mg/kg. The tetrahydrobiopterin is preferably administered orally.

The invention is supported by Reference Examples 1, 2, 3 and 4, and is illustrated by working Examples I, II, III, and IV and V which are set forth below.

The eNOS used in Reference Examples 1, 2, 3 and 4 was made as described in Martasek, P., et al., Biochem. Biophys. Res. Commn 219, 359–365 (1996).

REFERENCE EXAMPLE 1

Increasing concentrations of unlabeled pterins were incubated for 15 minutes at 22° C. with [$^3$]tetrahydrobiopterin ([$^3$H]BH$_4$), 10 pmoles, and eNOS, 3 pmoles, in binding buffer which is Tris.HCl, pH 7.5, (50 mM), and dithiothreitol (DTT) (1 mM), in a 100 microliter volume in each well in a 96-well filtration plate assay. The pterins used include 5,6,7,8-tetrahydrobiopterin (BH$_4$), 7,8-dihydrobiopterin (BH$_2$), 6-methyltetrahydrobiopterin (6 MePH$_4$) and sepiapterin. Data which are shown in FIG. 1 are mean±SEM values of triplicate determinations. Similar results were obtained in four separate experiments. In FIG. 1, the squares denote BH$_4$ for the naturally occurring (R)-stereoisomer of BH$_4$ and represent BH$_4$, the triangles represent BH$_2$, the diamonds represent 6 MePH$_4$, and the circles represent sepiapterin. In FIG. 1, the term "Inhibitor" in the horizontal legend means pterin analog and is generic for BH$_4$, BH$_2$, 6MePH$_4$ and sepiapterin. Incubations were carried out at the concentrations indicated by the data points in FIG. 1. This experiment is to compare the ability of the named pterins to compete for [$^3$H]BH$_4$ binding to eNOS. The results show that BH$_2$ and BH$_4$ bind with equal affinity to eNOS, so BH$_2$ formed in endothelial cells would effectively compete for binding to eNOS with BH$_4$ and stop nitric oxide production in the cases where it binds to eNOS (as indicated in Reference Example 3 and FIG. 3(b)).

REFERENCE EXAMPLE 2

Figure 2A:
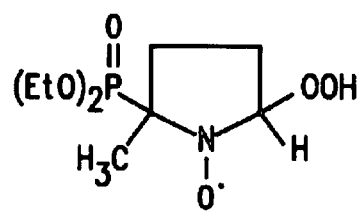
FIG. 2(*a*) shows electron paramagnetic resonance results that assess superoxide production by $BH_4$-bound eNOS in buffer.
Figure 2B:
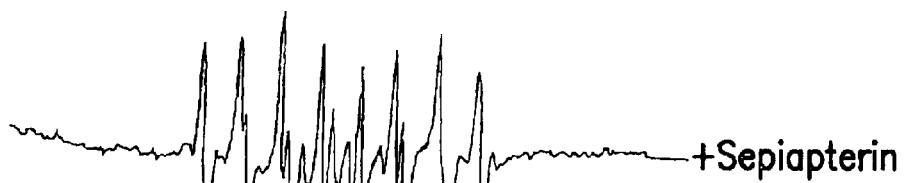
Figure 2C:
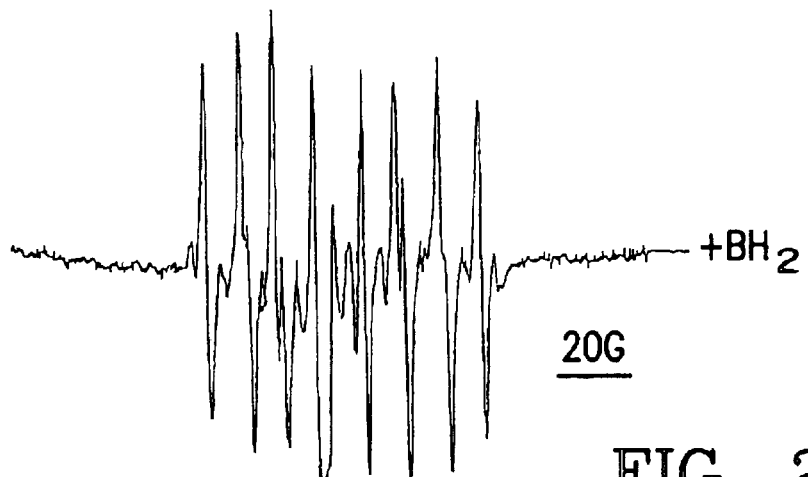

Assay buffer utilized contained HEPES (50 mM, pH 7.4), calcium (0.2 mM), calmodulin (10 μg/ml), NADPH (0.1 mM), L-arginine (0.1 mM), tetrahydrobiopterin (10 μM), DEPMPO (structure shown in upper right of FIG. 2(a)) (50 mM), and diethylenetriamine pentaacetic acid (DTPA) (0.1 mM). Included was 7 pmol eNOS. Incubation was for 15 min at 22° C. Subsequent addition was either of sepiapterin (50 μM) or BH$_2$ (1 mM). The DEPMPO functions as a probe (spin-trap) that selectively captures superoxide anion. Electron paramagnetic resonance (EPR) was carried out to determine superoxide production. EPR was carried out at microwave power of 2 mW, modulation amplitude 1G, time constant 0.128 seconds, scan rate 1.6 G/s, gain 1.25×10E5, number of scans 10. EPR shows an eight peak signal when the DEPMPO captures superoxide. Results are shown in FIGS. 2(a), 2(b) and 2(c). The line under 20G in FIG. 2(c) indicates that horizontal distance represents 20 gauss in FIGS. 2(a), 2(b) and 2(c). As shown in FIG. 2(a) eNOS does not produce superoxide when bound to BH$_4$. However, as shown in FIG. 2(c), subsequent addition of BH$_2$ can displace BH$_4$ and activate superoxide production. The results with sepiapterin (FIG. 2(b)) support the conclusion that binding of incompletely-reduced pterin, i.e., a dihydropterin such as sepiapterin, will activate superoxide production.

REFERENCE EXAMPLE 3

Figure 3A:
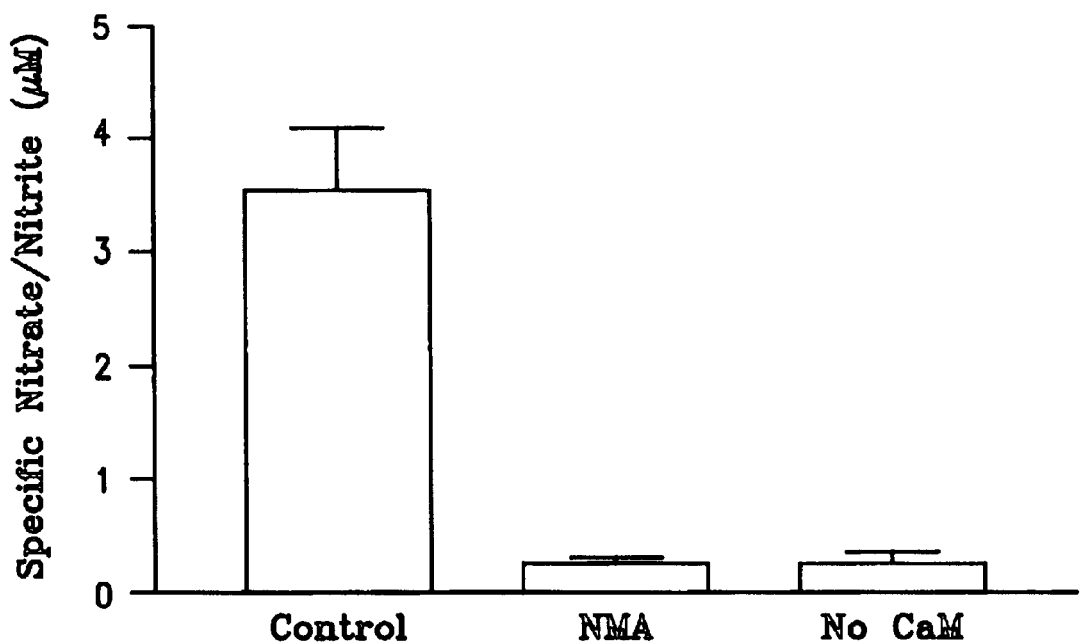
FIG. 3(*a*) is a graph showing $BH_4$-bound eNOS production of total nitrate/nitrite from arginine in assay buffer without $N^G$-methyl-L-arginine (NMA), denoted "Control"; with NMA denoted "NMA"; and after elimination of calmodulin, denoted "No CaM."
FIG. 3(d) is a graph showing $BH_2$-bound eNOS production of total nitrate/nitrite from $N^\omega$-hydroxyarginine in assay buffer without NMA, denoted "Control"; with NMA, denoted "NMA"; and after elimination of calmodulin, denoted "No CaM."
Figure 3B:
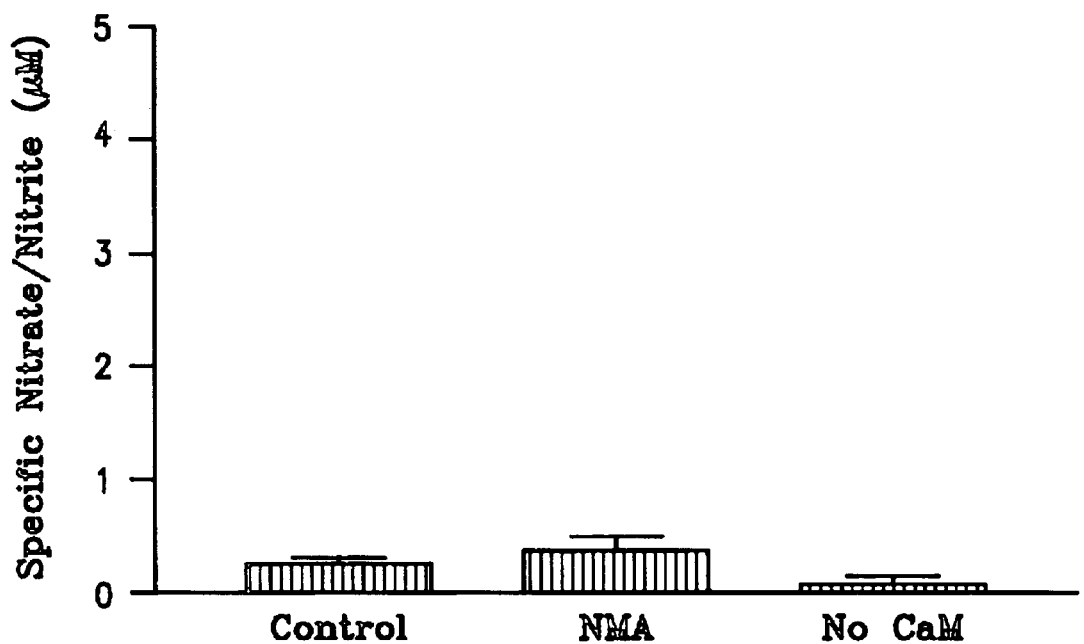
Figure 3C:
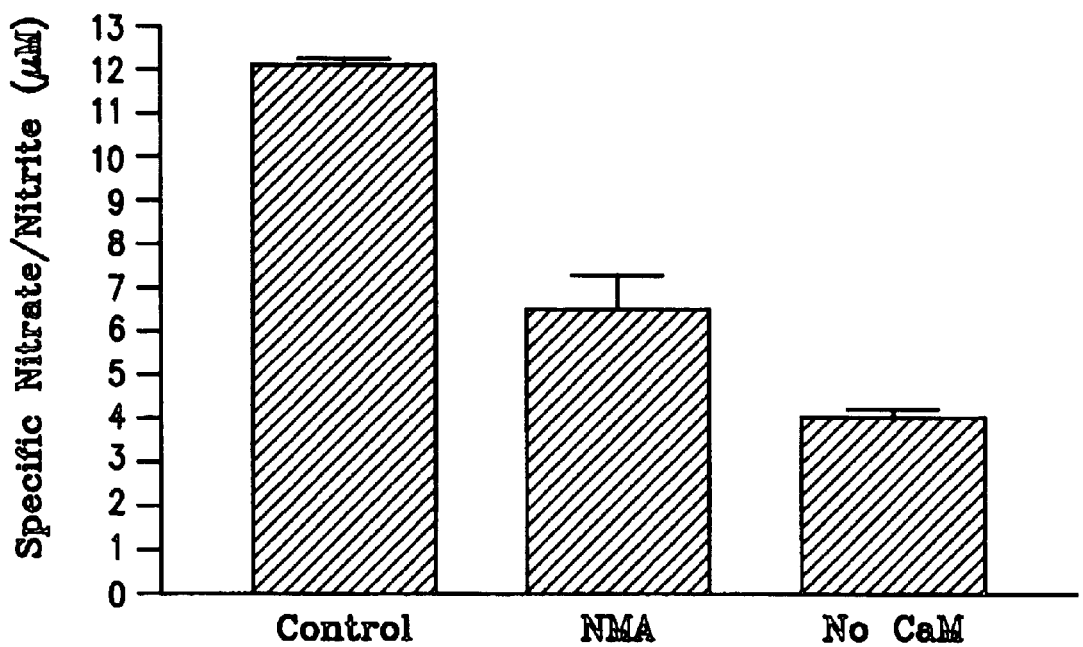
Figure 3D:
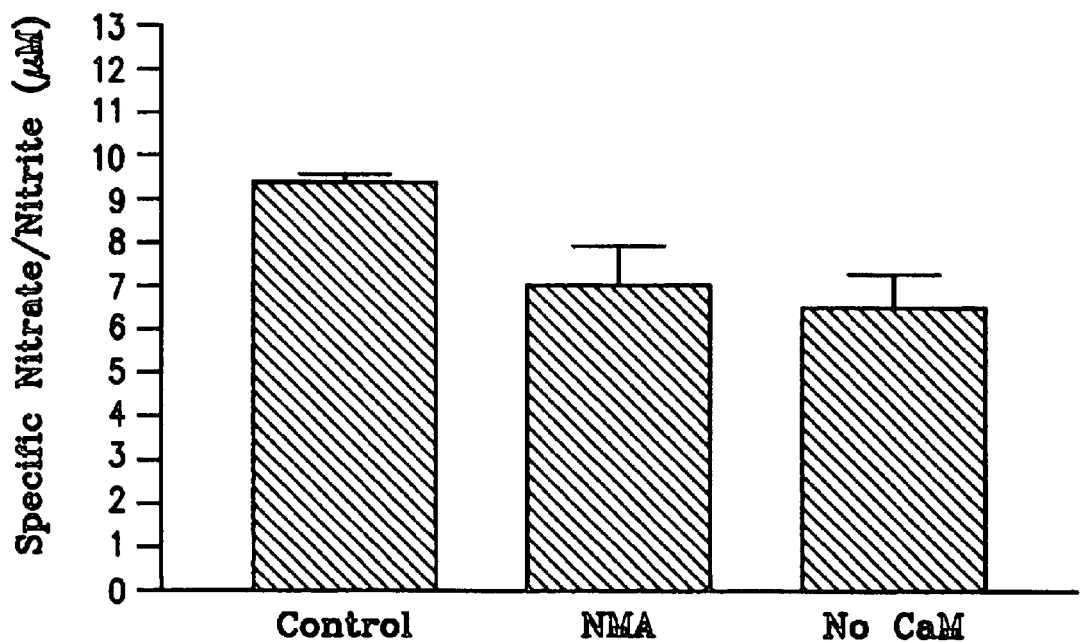

All samples were 100 microliter total volume and contained assay buffer (Tris.HCl pH 7.6 (50 mM), DTT (1 mM), calcium (100 μM), and calmodulin (100 nM)). In the assay buffer, eNOS (10 pmol), either BH$_4$ (10 μM) or BH$_2$ (10 μM), and either L-arginine (100 μM) or N$^\omega$-hydroxy-L-arginine (100 μM) were introduced. In some experiments, the nitric oxide synthase inhibitor N$^\omega$-methyl-L-arginine (NMA, 1 mM) was additionally added or the required NO synthase cofactor calmodulin was omitted (No CaM). Incubations were for 1 hour at 37° C. Total nitrate/nitrite (as a measure of nitric oxide) was measured by the Greiss assay as described in "Methods of Nitric Oxide Research," edited by Feelisch, M. and Stamler, J. S., John Wiley & Sons Ltd. (1996) at pages 491–497. Results are shown in FIGS. 3(a), 3(b), 3(c) and 3(d). FIG. 3(a) shows BH$_4$-bound eNOS production of total nitrate/nitrite from arginine. FIG. 3(b) shows BH$_2$-bound eNOS production of total nitrate/nitrite from arginine. FIG. 3(c) shows BH$_4$-bound eNOS production of total nitrate/nitrite from N$^\omega$-hydroxyarginine. FIG. 3(d) shows BH$_2$-bound eNOS production of total nitrate/nitrite from N$^\omega$-hydroxyarginine. Data represent means±SEM values of quadruplicate determinations. The results show that conversion to nitric oxide is by a different mechanism for arginine than for N$^\omega$-hydroxyarginine in that BH$_2$-bound eNOS does not cause production of nitric oxide from arginine but does cause production of nitric oxide from N$^\omega$-hydroxyarginine, whereas BH$_4$-bound eNOS causes production of nitric oxide from both arginine and N$^\omega$-hydroxyarginine. Although arginine conversion by BH$_4$-bound eNOS to nitric oxide is substantially blocked (>90%) by addition of NMA or removal of CAM, N$^\omega$-hydroxyarginine conversion to nitric oxide by BH$_2$-bound eNOS is little effected (<30%) by addition of NMA or removal of CAM.

Figure 4:
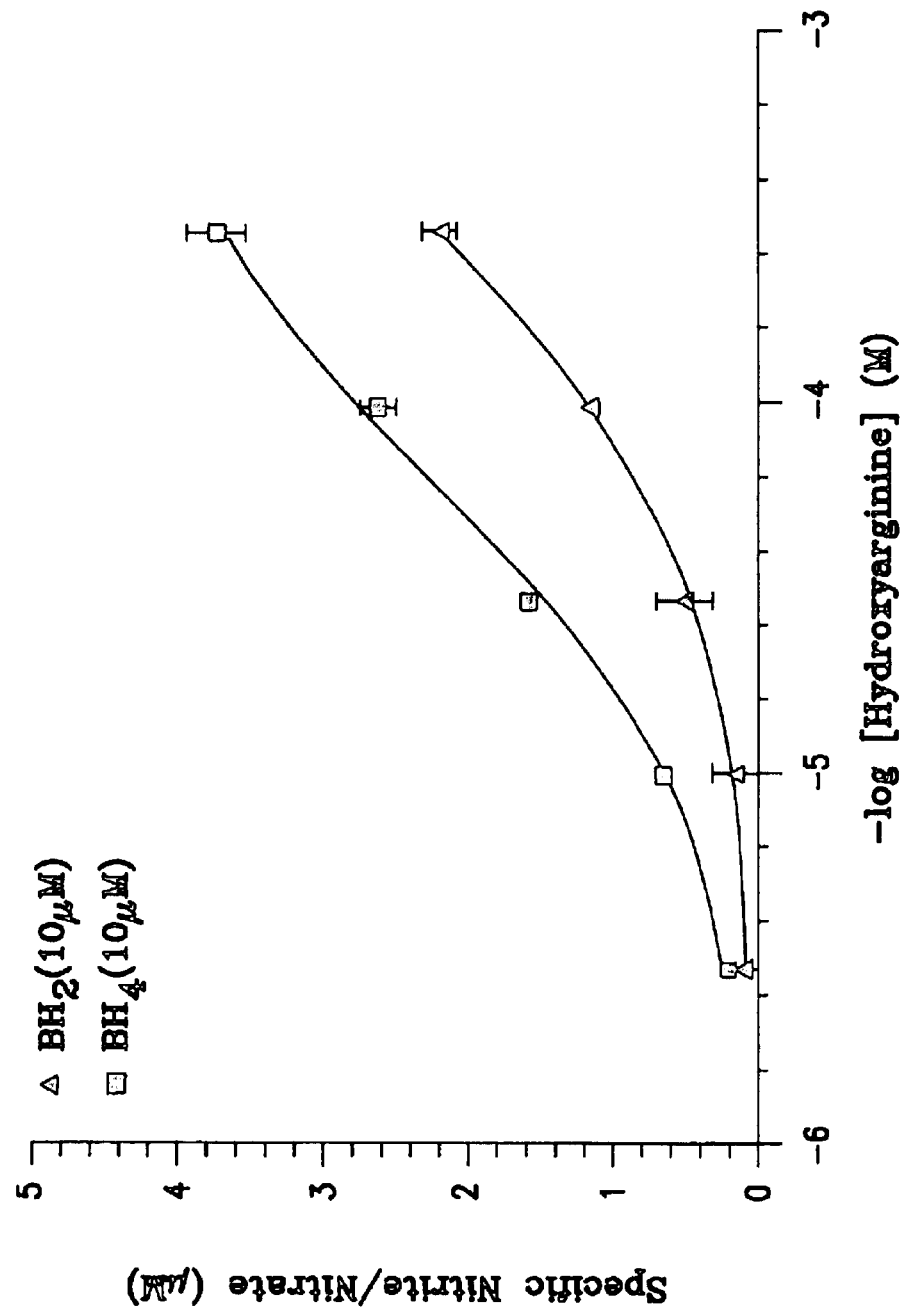
FIG. 4 is a graph containing curves showing concentration-dependence of nitric oxide synthesis from $N^\omega$- hydroxyarginine by $BH_2$-bound eNOS and by $BH_4$-bound eNOS.

REFERENCE EXAMPLE 4 eNOS (10 pmol) was preincubated for 30 minutes at 37° C. in the presence of either BH$_2$ (10 μM) or BH$_4$ (10 μM) in assay buffer (Tris.HCl pH 7.6 (50 mM), DTT (1 mM), calcium (100 μM) and calmodulin (100 nM)). Then N$^\omega$-hydroxy-L-arginine (denoted "Hydroxyarginine" in FIG. 4) was added (concentrations as disclosed in FIG. 4) and incubations were 100 microliter total volume and were allowed to proceed for 1 hour at 37° C. Nitric oxide production was assessed from accumulation of its stable oxidation products (nitrite and nitrate), quantified by a modified Greiss assay (reference recited in Reference Example 3). The results are shown in FIG. 4. Data are mean±SEM values of quadruplicate determinations. The results show concentration dependence of nitric oxide synthesis from N$^\omega$-hydroxyarginine by eNOS with either BH$_2$ or BH$_4$ as bound cofactor. Notably, N$^\omega$-hydroxy-L-arginine supports the production of nitrogen oxides by eNOS in the presence of either BH$_2$ or BH$_4$.

EXAMPLE I

A 40-year-old male with Type I diabetes presents with symptoms of pain in toes and loss of pink color (gray tissue tone) in toes. An ointment containing 1% by weight N$^\omega$-hydroxy-L-arginine is applied to the toes four times a day. Within 48 hours, pain diminishes and tissue becomes pinker. Blood perfusion is increased.

EXAMPLE II

A 60-year old male with coronary artery disease develops chest pain and electrocardiographic evidence of angina after 10 minutes on a treadmill at 3 mph and 5% incline. Within 90 minutes after an oral dose of 10 mg/kg of N$^\omega$-hydroxy- L-arginine, the subject is able to walk on the treadmill at 3 mph and 5% incline for 25 minutes without pain or evidence of arginine.

EXAMPLE III

A 60-year-old female has moderate hypertension (150/100 mm Hg) and elevated vascular resistance. One hour after receiving a single 10 mg/kg intravenous dose of $N^\omega$-hydroxy-L-arginine, mean arterial blood pressure is diminished by 14 mm Hg and systemic vascular resistance is reduced by 10%.

In the above Examples I, II, and III, a therapeutically effective amount of other hydroxyguanidine-containing agents can be substituted for the $N^\omega$-hydroxy-L-arginine to obtain the benefits of improved oxygenated blood flow to oxygen-deficient organs, lessened symptoms of coronary artery disease, reduced systemic vascular resistance, diminished progression of vascular stenosis and diminished inflammation.

EXAMPLE IV

A 55-year-old man suffers from type 2 diabetes (adult onset diabetes or insulin resistant diabetes), coronary artery disease and hypertension (a not uncommon composite of conditions), experiences a stroke resulting in acute left-sided paralysis owing to right middle cerebral artery occlusion. Surviving the stroke, the patient is placed on chronic oral therapy with $N^\omega$-hydroxy-L-arginine, 5 mg/kg every 4 hours, or a combination of this with L-arginine, 20 mg/kg every 4 hours. There is no recurrence of stroke within the next two years.

EXAMPLE V

A 60-year-old man exhibits mild hypertension (140/90 mm Hg) and angiographic evidence of coronary artery atherosclerosis and familial history of cardiovascular disease. He is treated with 5 mg/kg $N^\omega$-hydroxy-L-arginine every 4 hours orally as either free drug or in admixture with antioxidant agents and vitamins (e.g., ascorbate, alpha-tocopherol, vitamin B6, vitamin B12, folate (folic acid), carotenoids, coenzyme Q10, phytoestrogens (including isoflavonoids), selenium, butylated hydroxytoluene (BHT), butylated hydroxyanisole (BHA) and n-3 polyunsaturated fatty acids (PUFA)) with or without L-arginine supplementation (20 mg/kg every 4 hours). The mixture is delivered as a nutriceutical. Blood pressure normalizes to less than 130/80 mm Hg and angiographic evidence indicates atherosclerosis progression is less than 10% additional over the next five years.

When (6R)-5,6,7,8-tetrahydrobiopterin, 300 mg is substituted for the L-arginine in Examples IV and V, results of no recurrence of stroke within the next two years and normalized blood pressure, are obtained.

Variations

Variations in the above will be evident to those skilled in the art. Thus, the scope of the invention is defined by the claims.

What is claimed is:

1. A method for treating a disorder which is endothelial dysfunction associated with deficient nitric oxide bioactivity caused by oxidative stress in a patient in need thereof, comprising administering to the patient an endothelial dysfunction reversing or diminishing effective amount of an agent which is selected from the group consisting of nitric oxide bioactivity increasing hydroxyguanidines and pharmaceutically acceptable salts thereof.

2. The method of claim 1 where said agent is a nitric oxide bioactivity increasing compound having the formula:

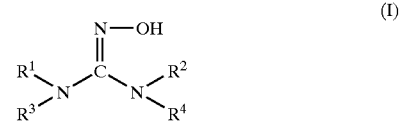

(I)

wherein $R^1$, $R^2$, $R^3$ and $R^4$ permit transport in cells and are the same or different and can be independently selected from the group consisting of hydrogen, amino, imino, alkyl, substituted alkyl, phenyl, substituted phenyl, cycloalkyl, benzyl, acyl, pyridyl, piperidyl, piperazyl, amino acid, lipid or carbohydrate and where $R^3$ and $R^4$ can optionally join to form a ring.

3. The method of claim 1 where a therapeutically effective amount of L-arginine is also administered.

4. The method of claim 1 where a therapeutically effective amount of tetrahydrobiopterin is also administered.

5. The method of claim 2 where the disorder is the endothelial dysfunction of coronary artery disease.

6. The method of claim 2 where the disorder is the endothelial dysfunction of atherosclerosis.

7. The method of claim 2 where the disorder is the endothelial dysfunction of mild hypertension.

8. The method of claim 2 where the disorder is the endothelial dysfunction of moderate hypertension.

9. A method for treating Type-1 diabetes involving endothelial dysfunction associated with deficient nitric oxide bioactivity caused by oxidative stress in a patient in need thereof, comprising administering to the patient a therapeutically effective amount of a nitric oxide bioactivity increasing compound having the formula:

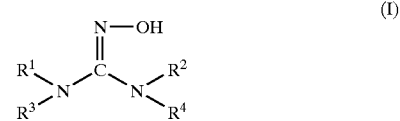

(I)

wherein $R^1$, $R^2$, $R^3$ and $R^4$ permit transport in cells and are the same or different and can be independently selected from the group consisting of hydrogen, amino, imino, alkyl, substituted alkyl, phenyl, substituted phenyl, cycloalkyl, benzyl, acyl, pyridyl, piperidyl, piperazyl, amino acid, lipid or carbohydrate and where $R^3$ and $R^4$ can optionally join to form a ring.

10. A method for treating Type-2 diabetes involving endothelial dysfunction associated with deficient nitric oxide bioactivity caused by oxidative stress in a patient in need thereof, comprising administering to the patient a therapeutically effective amount of a nitric oxide bioactivity increasing compound having the formula:

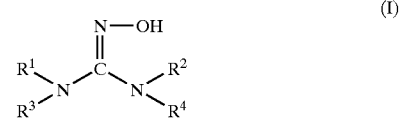

(I)

wherein $R^1$, $R^2$, $R^3$ and $R^4$ permit transport into cells and are the same or different and can be independently selected from the group consisting of hydrogen, amino, imino, alkyl, substituted alkyl, phenyl, substituted phenyl, cycloalkyl, benzyl, acyl, pyridyl, piperidyl, piperazyl, amino acid, lipid or carbohydrate and where $R^3$ and $R^4$ can optionally join to form a ring.

11. The method of claim 2 where the nitric oxide bioactivity increasing compound is not a substrate for $BH_4$-bound eNOS.

12. The method of claim 2 where the nitric oxide bioactivity increasing compound generates nitric oxide in the presence of $BH_2$-bound eNOS.

13. The method of claim 2 where the agent is $N^\omega$-hydroxy-L-arginine.

14. The method of claim 13 where a therapeutically effective amount of L-arginine is also administered.

15. The method of claim 13 where a therapeutically effective amount of tetrahydrobiopterin is also administered.

16. The method of claim 1 where the disorder is the endothelial dysfunction of hypertension.

17. The method of claim 9 where the agent is $N^\omega$-hydroxy-L-arginine.

18. The method of claim 10 where the $N^\omega$-hydroxy-L-arginine.

* * * * *